United States Patent [19]

Costa et al.

[11] 4,026,288
[45] May 31, 1977

[54] SYRINGE INJECTING DEVICE

[75] Inventors: Roger Costa, Somerset, Mass.; Lawrence T. French, Jr., East Providence, R.I.

[73] Assignee: Insulin Injector Inc., East Providence, R.I.

[22] Filed: Oct. 21, 1975

[21] Appl. No.: 624,337

[52] U.S. Cl. .............................. 128/218 F; 124/37
[51] Int. Cl.² .......................................... A61M 5/20
[58] Field of Search ............ 128/DIG. 1, DIG. 11, 128/218 F, 216, 214 F, 215, 236; 124/16, 37

[56] References Cited

UNITED STATES PATENTS

| | | | |
|---|---|---|---|
| 1,852,401 | 4/1932 | DeCamps | 124/37 X |
| 2,295,849 | 9/1942 | Kayden | 128/218 F |
| 2,305,176 | 12/1942 | Littman | 124/16 X |
| 2,472,116 | 6/1949 | Maynes | 128/218 F |
| 2,918,063 | 12/1959 | Tucker | 128/218 F |
| 3,029,539 | 4/1962 | Glass et al. | 124/16 X |
| 3,702,608 | 11/1972 | Tibbs | 128/218 F |
| 3,880,163 | 4/1975 | Ritterskamp | 128/218 F |

Primary Examiner—Clifford D. Crowder
Attorney, Agent, or Firm—Barlow & Barlow

[57] ABSTRACT

A syringe injecting device comprising a body with a slideway therein which receives a syringe carriage biased into one position by a spring and reciprocal in said slideway. A handle extends from the body and there is a communication between the carriage for the syringe and a gear in the handle, which gear is controlled by a latch having a detent which may be released by a trigger from permitting the carriage to be impelled forward under spring action to insert the needle of the syringe into a body.

2 Claims, 4 Drawing Figures

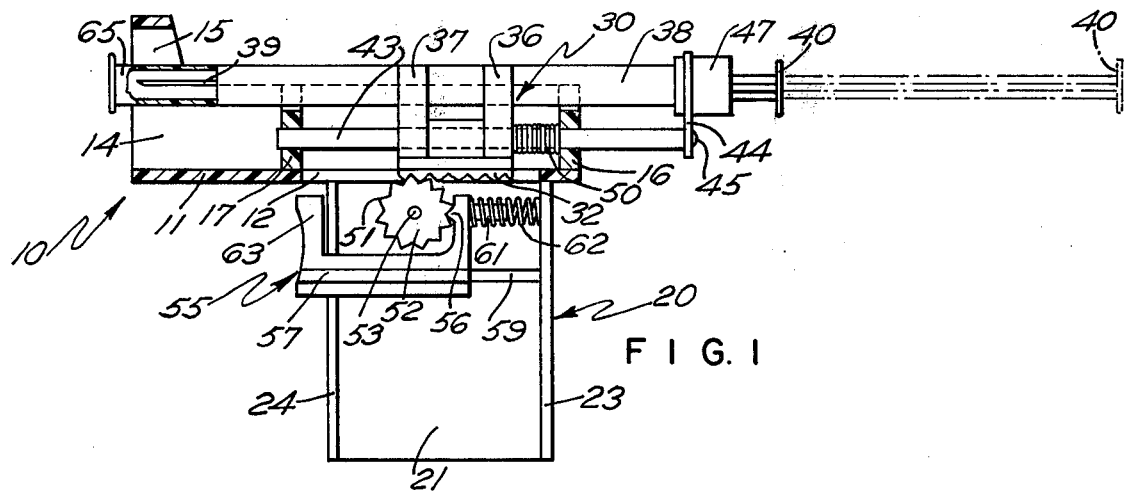
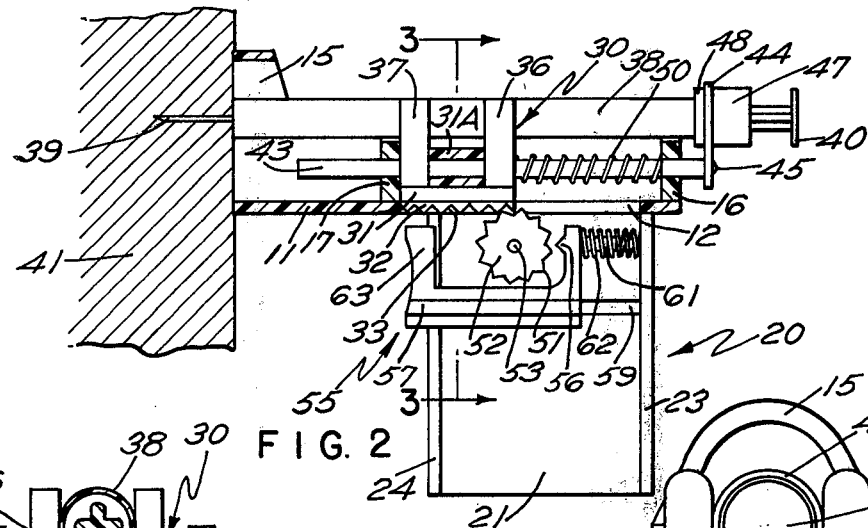
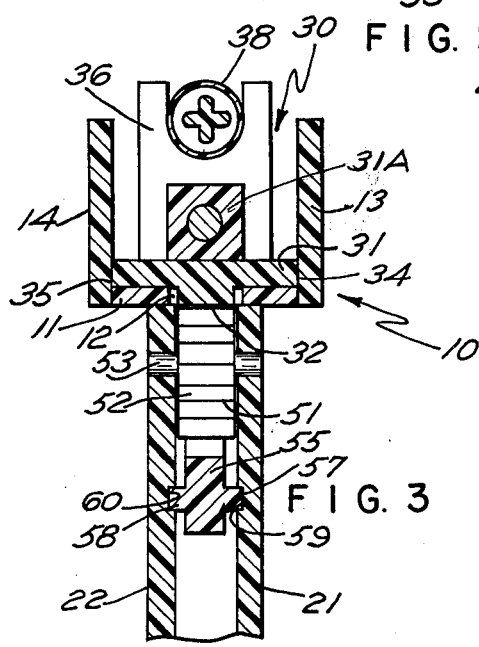
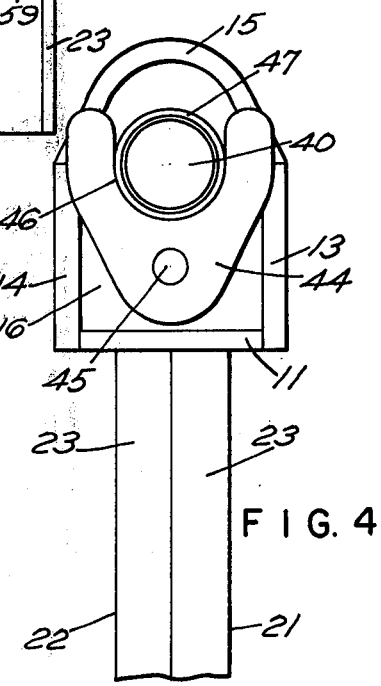

SYRINGE INJECTING DEVICE

BACKGROUND OF THE INVENTION

Heretofore, syringe injecting devices have been somewhat complicated in the carrying of the syringe and the mechanism for releasing the part that carries the syringe to cause the needle to be quickly impelled into the body which is to receive the contents of the syringe. Primarily, the devices have all utilized combination insertion and injecting mechanisms which multiply the parts and can be a source of malfunction. Examples of prior art designs are found in U.S. Pat. Nos. 2,295,849 and 2,918,063 and British Specification No. 1,242,060.

SUMMARY OF THE INVENTION

There is a plastic body with a handle extending therefrom, both of which are hollow. In the body there is a slidable carriage which mounts the syringe which is to be used for injection into the body. The carriage has a tongue with teeth on its underside which projects into or communicates with a part in the handle, and in the handle there is a gear which engages this toothed tongue or rack and controls this movement. A latch engages the gear so as to prevent it from rotating and consequently prevents a spring, which urges the carriage forward, from injecting the syringe. This latch has a fingerpiece or trigger which extends through the handle and may be operated by the finger of the user to compress a spring which urges it outwardly so as to release the gear and permit the spring which actuates the carriage to inject the syringe into the body. There is thus two sliding parts in a rigid housing; the sliding parts and housing may be molded from plastic and the device simply assembled with simple connecting parts.

DESCRIPTION OF THE DRAWINGS

FIG. 1 is a longitudinal sectional view of an elevation of the device with the syringe in position and a cover for the needle of the syringe;

FIG. 2 is a similar view but shows the carriage driven forward by a spring and the needle penetrating a body with which it is to be used and also showing the latch for controlling the carriage in its release position;

FIG. 3 is a section on line 3—3 of FIG. 2; and

FIG. 4 is a rear end view of the device.

DESCRIPTION OF THE PREFERRED EMBODIMENT

Referring to the drawing, the body designated generally 10 is generally trough-shaped (see FIG. 3) providing a slideways for a carriage 30. This body has a bottom wall 11 with a longitudinal slot 12 therein that extends lengthwise of the body for a portion of its length (see FIG. 2). Side walls 13 and 14 extend upwardly from the bottom wall 11 the full length of the bottom wall and are joined by an arch bridge 15 at the forward end of the body. There are abutment walls 16 and 17 spaced from each other, the abutment wall 16 being at the end of the body and providing an end wall, and the abutment wall 17 being midway of the length of the body as seen particularly in FIG. 2.

A handle designated generally 20 comprises opposite side walls 21 and 22 seen best in FIG. 3 which have edge flanges 23 and 24 at their opposite ends which abut as shown in FIG. 4 so as to maintain the walls 21 and 22 in spaced relation as shown in FIG. 3.

A carriage generally designated 30 is located in the trough of the body and comprises generally a bottom wall 31 that has mounted thereon a guide block 31A and spaced resilient gripping arms 36, 37. The edges of the bottom wall at 34, 35 have sliding engagement with the side walls 13 and 14 of the body, and extending centrally below the bottom wall is a tongue 32 that is provided with rack teeth 33, and this protrudes through longitudinal slot 12 into the handle area. A rod 43 is gripped in the block 31A and carries a U-shaped plate 44 rivetly secured as at 45. A syringe 38 is provided with the usual finger flanges 48, and the body is gripped in arms 36, 37 while the flanges 48 are received abutting the inner side of plate 44. In this position the needle 39 of the syringe will protrude beyond the arched bridge 15.

The carriage is mounted between the abutment walls 16 and 17 as seen in FIG. 2, and a spring 50 encircles the rod 43. Thus, one end of the spring engages the abutment plate 16, while the other end of the spring engages the end wall 36 of the carriage 30, and, thus, when the carriage is moved to the right as shown in FIG. 2, the spring is compressed. As the carriage is moved to the right as seen in FIG. 2, the rack teeth 33 which engage the teeth 51 of the gear 52 rotate this gear on its pivot 53 which is fixed in the handle 20. A latch 55 having a detent 56 is provided with ribs 57 and 58 extending from either side thereof into recesses 59 and 60 in the walls 21 and 22 of the handle so as to be guided thereby in its sliding movement. A spring 61 extending about a guide pin 62 on the latch engages the flanges 23 of the handle and urges the slide to the left as shown in FIG. 2 so that the detent 56 will engage the teeth of the gear 52 and stop it from rotation in either direction, thus locking the carriage in its position of sliding until the detent is released. A fingerpiece or trigger 63 is located on the forward side of the latch and protrudes through the flanges 24 of the handle so as to be in an exposed position for operation by the finger of the user of the device.

In operation, the carriage will be moved to its forward position by operating the fingerpiece or latch to release the gear 52 and permit the spring 50 to move the carriage to this forward position. The cover 65 over the needle 39 of the syringe 38 will be removed, and the needle will be placed into the liquid which is to be injected, and then the plunger 40 will be withdrawn as shown in dotted lines FIG. 1 to draw into the syringe the liquid which is to be injected. During this operation, the detent and the plate 44 keep the syringe in position and prevent the syringe sliding in the carriage. The carriage will then be retracted into the position shown in FIG. 1 by depressing the fingerpiece and pulling on flanges 48 so that the spring 50 is compressed, and then the latch 55 may be released to its forward position with its spring 62 expanded. The cover 65 having been removed, the syringe is in position now for injection and may be placed against the portion of the body 41 which is to be injected as shown in FIG. 2 and then the latch may be released by pressing on the trigger or fingerpiece 63 so as to remove the detent 56 from the gear, thus allowing the spring 50 to force the carriage forwardly and at the same time rotating the gear, so that the needle will be injected into the person who is to receive the contents of the syringe. After the needle 39 has penetrated the body 41, the desired amount of contents of the syringe are discharged by forcing the plunger 40 into the syringe body in the usual manner.

We claim:

1. A syringe injecting device comprising a body provided with a slideway, a carriage slidable in said slideway, a spring for urging said carriage forwardly in said body, a handle extending from said body, said carriage having a rack extending from said slideway, means in said handle for controling the slidable movement of said carriage under influence of said spring, said means including a fingerpiece extending from said handle, a gear rotatably mounted in said handle and engaging said rack, and latch having a positive detent engaging said gear to lock it against rotation in either direction, said fingerpiece operating said latch, said latch being urged toward said gear by a spring, said carriage having means to carry a syringe.

2. A syringe injector device comprising
a body having
spaced side walls,
spaced abutment walls spanning said side walls and
a bottom wall having a slot therein extending parallel to said side walls, a handle having walls extending from said bottom wall, one on either side of said slot therein,
a carriage slidable on said bottom wall guided by said side walls and between said abutment walls and provided with a tongue extending into said slot, said tongue having teeth on its under surface,
a spring acting between said carriage and one abutment wall to urge said carriage forwardly toward the other abutment wall,
said carriage having means to carry a syringe,
a gear in said handle rotatable on a fixed pivot and engaging the teeth of said tongue,
a latch slidably mounted in said handle having a detent to engage said gear and lock it against rotation in either direction, a spring to urge said latch and detent into engagement with said gear,
said latch having a finger engaging portion extending outwardly of said handle in a position to be engaged for sliding said latch to release said detent from said wheel and permit said gear to rotate and said carriage to move forwardly under influence of said spring acting on said carriage.

* * * * *